United States Patent [19]

Kummann

[11] Patent Number: 4,676,812
[45] Date of Patent: Jun. 30, 1987

[54] PROCESS FOR THE SEPARATION OF A $C_{2+}$ HYDROCARBON FRACTION FROM NATURAL GAS

[75] Inventor: Paul Kummann, Munich, Fed. Rep. of Germany

[73] Assignee: Linde Aktiengesellschaft, Wiesbaden, Fed. Rep. of Germany

[21] Appl. No.: 797,061

[22] Filed: Nov. 12, 1985

[30] Foreign Application Priority Data

Nov. 12, 1984 [DE] Fed. Rep. of Germany ....... 3441307

[51] Int. Cl.$^4$ ................................................. F25J 3/02
[52] U.S. Cl. ......................................... 62/24; 62/28; 62/38
[58] Field of Search ..................... 62/24, 28, 38, 39, 27

[56] References Cited

U.S. PATENT DOCUMENTS

| | | | |
|---|---|---|---|
| 2,557,171 | 6/1951 | Bodle et al. | 62/39 |
| 2,823,523 | 2/1958 | Eakin et al. | 62/39 |
| 3,375,673 | 4/1968 | Cimler et al. | 62/39 |
| 3,416,323 | 12/1968 | Heinik | 62/39 |
| 3,559,417 | 2/1971 | Hoffman | 62/24 |
| 4,061,481 | 12/1977 | Campbell et al. | 62/38 |
| 4,203,741 | 5/1980 | Bellinger et al. | 62/38 |
| 4,274,850 | 6/1981 | Becker | 62/24 |

Primary Examiner—Ronald C. Capossela
Attorney, Agent, or Firm—Millen & White

[57] ABSTRACT

In a process for separating $C_{2+}$ hydrocarbons from natural gas under elevated pressure, by rectification wherein the temperature and pressure required for rectification are attained by heat exchange and two-stage engine expansion, the rectification being conducted between the two expansion stages, the overhead methane fraction obtained during rectification is heated to ambient temperature, then engine expanded, and again heated to ambient temperature. The peak cold for rectification is essentially produced by engine expansion of the raw gas to be fractionated.

21 Claims, 2 Drawing Figures

PROCESS FOR THE SEPARATION OF A $C_{2+}$ HYDROCARBON FRACTION FROM NATURAL GAS

BACKGROUND OF THE INVENTION

This invention relates to a rectification process for the separation of $C_{2+}$ hydrocarbon fraction from natural gas under elevated pressure, and in particular to a process wherein the temperature and pressure values employed for rectification are obtained by heat exchange and two-stage engine expansion and wherein the rectification is performed between the two expansion stages.

A process of the above-mentioned type has been described in U.S. Pat. No. 4,274,850. In this process, the essential feature requires that the peak cold for the rectification be produced by engine expansion of the overhead product from the rectification step whereas cold is produced at an intermediate temperature level by engine expansion of the natural gas to be fractionated. Rectification takes place, in the presence of limited amounts of $CO_2$, at a sufficiently high pressure so as to avoid freezing out carbon dioxide. This process, if performed without the use of external refrigeration, requires a higher initial pressure of the natural gas, e.g., generally at least 5 to 15 bar higher than in the process of the invention, the exact value depending upon the composition of the natural gas.

SUMMARY OF THE INVENTION

An object of one aspect of the present invention, therefore, is to provide a process and apparatus of the type discussed having an improved refrigeration capacity so that $C_{2+}$ separation can be attained without the utilization of external refrigeration even in case of a relatively lower initial pressure of the natural gas to be fractionated.

Upon further study of the specification and appended claims, further objects and advantages of this invention will become apparent to those skilled in the art.

To attain these objects, there is provided a process comprising precooling the natural gas to-be-rectified and engine-expanding resultant precooled natural gas to produce the peak cold for the rectification step.

Advantageous additional steps comprise passing the overhead product from the rectification step in indirect heat exchange relationship with natural gas to be cooled, thereby heating said overhead product to about the inlet temperature of the natural gas to be fractionated, then passing resultant heated overhead product to the second expansion stage so as to cool said overhead product, and passing resultant cooled overhead product in indirect heat exchange relationship with natural gas to be cooled so as to heat the overhead product to approximately the inlet temperature of the natural gas to be fractionated.

In contrast to the method known from U.S. Pat. No. 4,274,850 the peak cold is provided according to this invention by engine expansion of the natural gas to be fractionated, and precooling is accomplished by engine expansion of the overhead product from the rectification. In this connection, an important feature of the invention resides in that the overhead product is introduced, approximately at the inlet temperature of the natural gas to be fractionated into an expansion engine since at this relatively high temperature level a very high refrigerating power can be obtained. The inlet temperature of the natural gas to be fractionated is understood to mean, in this context, the temperature of the previously optionally compressed, dried and/or desulfurized natural gas prior to the first heat exchange stage. This inlet temperature is generally the ambient temperature, for example between 285° and 320° K. The inlet pressure, on the other hand, is generally about 25 to 75, especially about 30 to 60 bar. The overhead product from the rectification is heated prior to expansion substantially to the inlet temperature of the natural gas to be fractionated. The temperature differences between these two streams are conventional to indirect heat exchange between two streams, i.e., normally below 10° K., and in most instances below 7° K., generally in the range of 3° to 7° K.

Expansion of the heated overhead product is advantageously conducted so as to cool the gas by preferably 50° to 90° K., especially by 65° to 80° K. during this step, so that temperatures of about 220°–240° K. are generally attained. The overhead product is introduced into the second expansion stage at a temperature of about 260°–310° K., preferably 270°–305° K. However, the attainable cooling effect in an individual case depends, in essence, on the pressure difference available, i.e., on the difference between the rectifying pressure and the set discharge pressure of the overhead fraction. Rectification can be performed in general under a pressure of 10–22 bar, preferably 15–18 bar. A use of higher pressures, for example between 20 and 25 bar, does increase, with constant discharge pressure, the pressure gradient available and thus the refrigeration effect attainable, but at the same time the possibility of efficiently heating the column by cooling raw gas (intermediate heating) is lowered so that the use of such higher pressure proves to be disadvantageous to the process as a whole in many instances. On the other hand, there are many cases where a relatively high pressure of, for example, 15–20 bar is to be maintained, especially in the fractionation of natural gas that contains carbon dioxide, in order to safely avoid freezing out relatively high-boiling components, such as carbon dioxide.

Ordinarily, the natural gas to be fractionated, after precooling, but before engine expansion, is subjected to a condensate phase separating step wherein the condensate fraction rich in heavy components is introduced, after passage through a pressure-reducing valve, directly into the rectification column while only the residual gas phase is subjected to engine expansion. It is especially advantageous to effect the precooling of the natural gas to be fractionated and the condensate phase separation in two stages. In this connection, the first condensate phase separation step can be conducted after cooling of the natural gas in indirect heat exchange against engine-expanded overhead product from the rectification column, whereas, during the further cooling of the natural gas in indirect heat exchange against overhead product to be heated, additional components are condensed which are separated in a second phase separator and the resultant uncondensed proportion of natural gas is then engine-expanded just before it is passed into the rectification column. The two stage condensate phase separation is advantageous because it is thereby avoided that heavier components which condense at higher temperature are unnecessarily subcooled which would increase the size of heat exchangers. On the other hand, in case of a one-stage condensate phase separation, the presence of heavy components increases the boiling temperature on the affected plates in the rectification column and thereby negatively affects intermediate reboiling.

In an advantageous further development of the process according to this invention, the condensate separated in the second phase separator is first subcooled by about preferably 45° to 30° K. to the head temperature of the column and then passed via a pressure reducing valve into the rectification column. By subcooling the condensate fraction to the head temperature of the rectification column in indirect heat exchange against process streams to be heated, it is thus made possible, on the one hand, to produce a portion of the peak cold and, on the other hand, this aspect of the process permits introduction of the condensate into the column at a point above the point of introduction of the engine-expanded natural gas into the rectification column. By the latter positioning of the feeds, a reflux or scrubbing effect is provided so that an additional yield of $C_{2+}$ fraction is obtained from the engine-expanded natural gas fed into the column. Besides, this version of the process makes it possible to effect engine expansion of the natural gas at a slightly higher temperature, e.g., about 2° to 5° K. higher than would be possible without subcooling of the condensate fraction. The resultant, somewhat higher operating temperature of the expansion engine leads, in turn, to improved refrigerating efficiency. The difference between the two feed points amounts generally to about 3 to 6 theoretical plates.)

BRIEF DESCRIPTION OF THE DRAWINGS

Various other objects, features and attendant advantages of the present invention will be more fully appreciated as the same becomes better understood when considered in connection with the accompanying drawings, in which like reference characters designate the same or similar parts throughout the several views, and wherein.

DETAILED DESCRIPTION OF THE DRAWINGS

Figure 1:
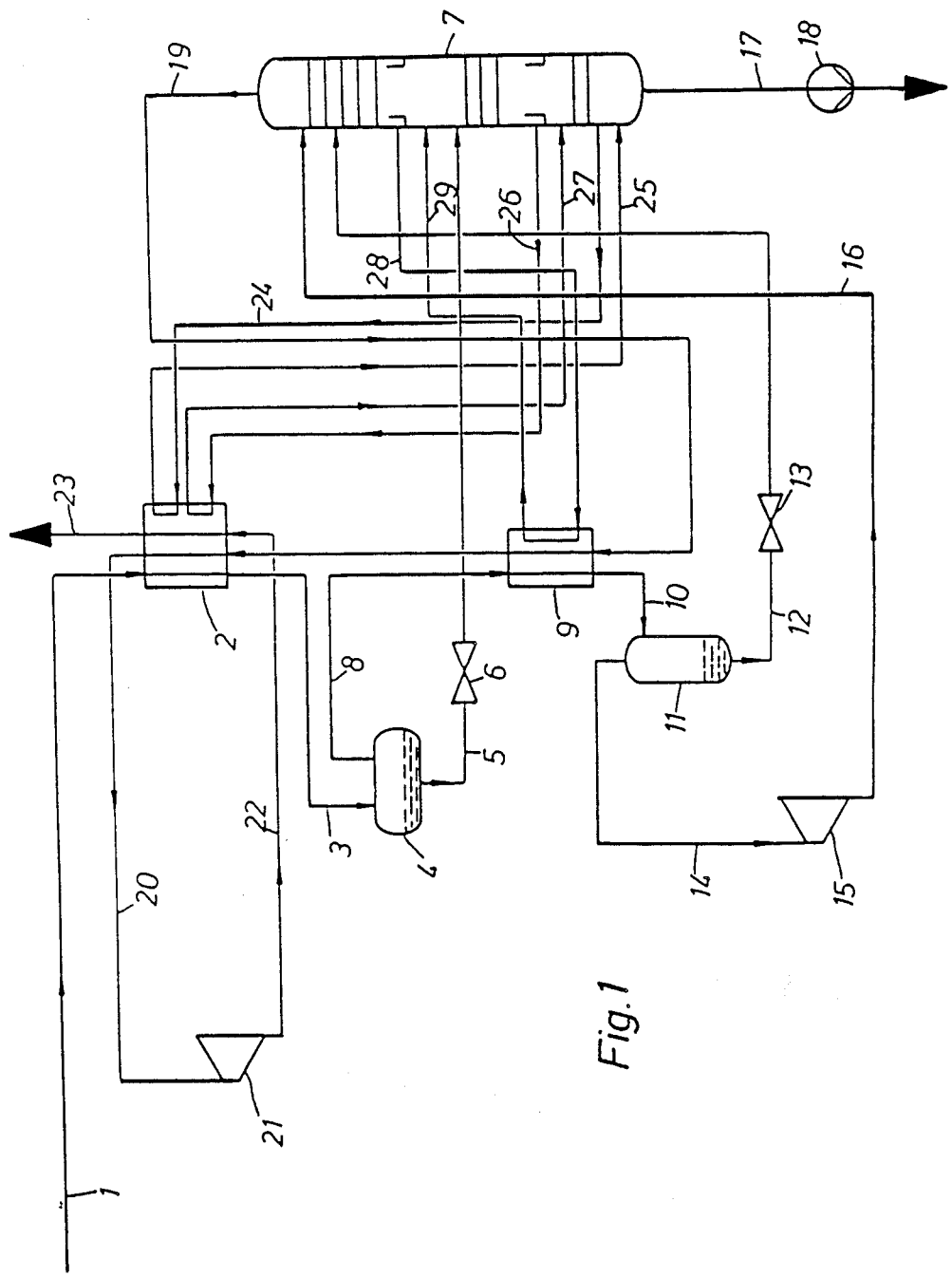
FIG. 1 shows a first comprehensive embodiment of the process of this invention.

In the embodiment shown in FIG. 1, preliminarily purified and compressed natural gas is introduced via conduit 1 at ambient temperature, cooled to about 230° K. in heat exchanger 2, and thereafter fed via conduit 3 to a first phase separator 4 to separate condensate formed during heat exchange. The condensed components, essentially higher-boiling ingredients of the natural gas, are withdrawn via conduit 5, pressure-reduced to rectification pressure in valve 6, and introduced into a middle zone of the rectifying column 7. The uncondensed components of the natural gas are discharged from phase separator 4 via conduit 8, further cooled in heat exchanger 9 to about 210° K., and subsequently introduced via conduit 10 into a second phase separator 11. The components condensed in the second heat exchange step are passed via conduit 12 and pressure-reducing throttle valve 13 into the upper zone of the rectifying column 7. The feed points of this condensate, as well as the condensate withdrawn via conduit 5, into the rectifying column 7 are determined in the usual way in correspondence with the temperature and equilibrium curves within the rectifying column 7. The uncondensed proportion of the natural gas is withdrawn from phase separator 11 via conduit 14 and engine expanded in a turbine 15 to the pressure of the rectification column. The natural gas is cooled during expansion, for example to temperatures around 170° K. The expanded fraction is introduced via conduit 16 to the head of the rectifying column 7. The expandet outlet stream has a liquid fraction of generally 15 to 25% depending on the pressure ratio of the expanded and on gas composition. The liquid fraction supplies the peak cold for rectification.

The bottoms fraction obtained during rectification, i.e., the $C_{2+}$ hydrocarbon fraction, is withdrawn via conduit 17 and optionally brought to a higher discharge pressure by means of a pump 18 before this process product is removed. At the head of the rectifying column 7, a fraction is obtained which is essentially free of $C_{2+}$ hydrocarbons; this fraction is withdrawn via conduit 19 and heated in heat exchangers 9 and 2 to the inlet temperature of the natural gas against natural gas to be cooled. The thus-heated gas then passes via conduit 20 into a second expansion turbine 21 wherein it is expanded essentially from the rectification pressure to a lower discharge pressure. During expansion, taking place, for example, from about 17 to about 4.5 bar, the gas is cooled down to about 230° K. and is again conducted via conduit 22 through heat exchanger 2 where before it is finally discharged to a consumer via conduit 23, contributes substantially toward the preliminary cooling of the entering natural gas.

In order to assist in the preliminary cooling of the natural gas in heat exchanger 2, on the one hand, and for heating the lower portion of the rectifying column 7, on the other hand, in a preferred embodiment, liquid is withdrawn from preferably the second plate via conduit 24 and, after being heated in heat exchanger 2, is returned via conduit 25 into the sump of the column. In a similar manner a fraction withdrawn via conduit 26 from the lower zone of the rectifying column 7, is heat exchanged in exchanger 2 and then recycled into the rectifying column via conduit 27. Finally, further intermediate heating is provided for the rectifying column 7, by withdrawing liquid from an upper zone via conduit 28 and, after being heated in heat exchanger 9, returning resultant fluid to the column via conduit 29. The refrigeration obtained in heat exchanger 9 from this stream is likewise transferred to the natural gas to be cooled. In all cases, the fluid returned to the column is at least partially vapor.

Figure 2:
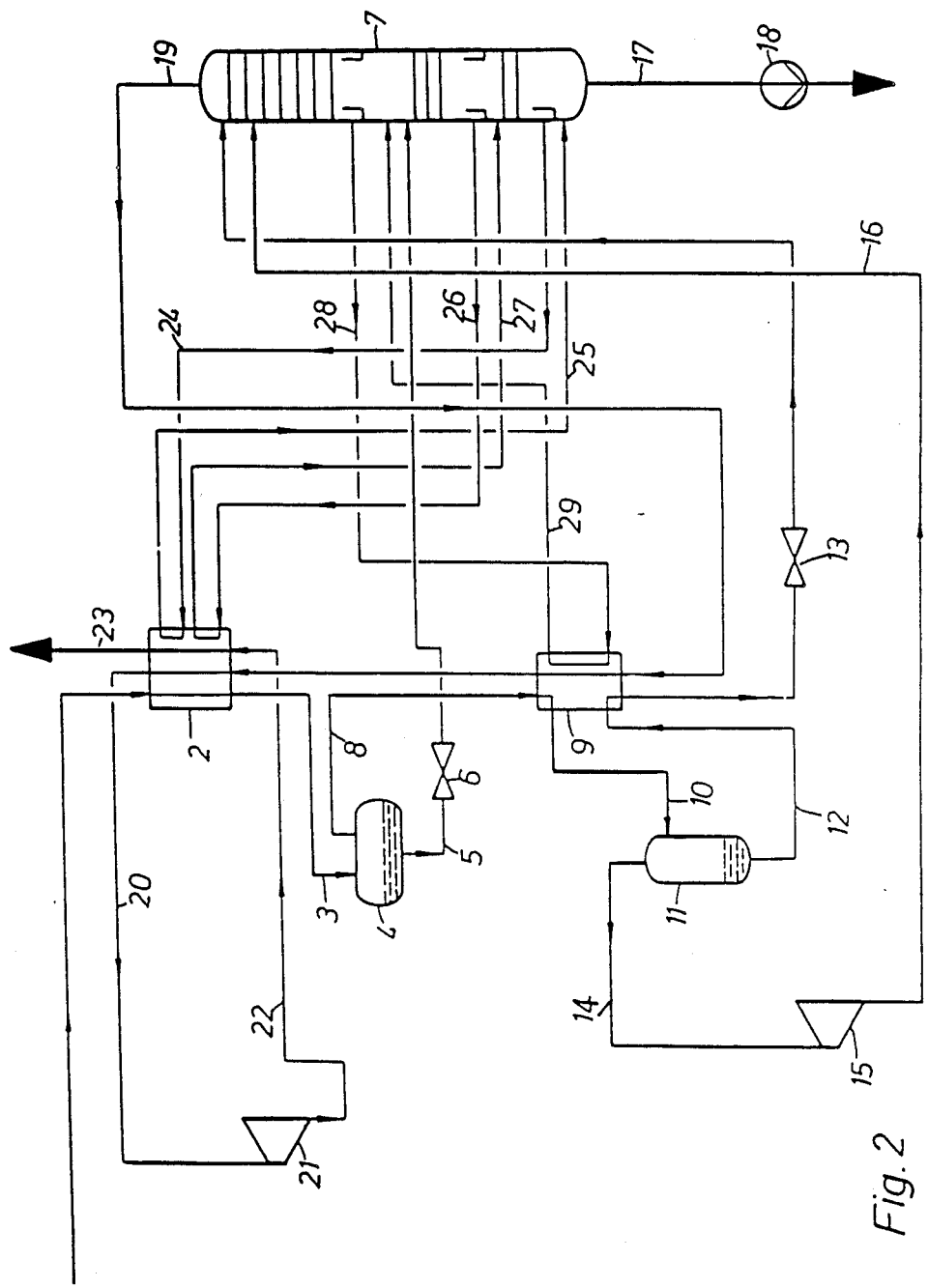
FIG. 2 shows a preferred comprehensive embodiment of the process of this invention.

The embodiment illustrated in FIG. 2 differs from that described above merely in that the condensate obtained in the second separator 11 is not conducted directly into the rectifying column 7 after expansion, but rather this condensate is first subcooled in heat exchanger 9. After throttle expansion in 13 to the pressure of the rectifying column 7, the condensate is fed to the head of the rectifying column, its feed point lying above the feed point for the gas expanded in turbine 15 and introduced via conduit 16. The introduction of subcooled condensate at the head of rectifying column 7 has the result that additional $C_{2+}$ hydrocarbons are scrubbed out of the vapor rising toward the column head, thereby obtaining a higher overall yield. On the other hand, if an unchanged yield is desirable, then this mode of operation makes it possible to provide more favorable operating conditions for the turbine 15 since it can be run at somewhat higher temperatures, and this, in turn, leads to a higher turbine efficiency and/or to a reduced initial pressure.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Kelvin and all parts and percentages are molar; unless otherwise indicated.

In a concrete example, practicing the process of FIG. 2, purified natural gas containing 78.3% of methane, 7.3% of ethane, 7.9% of propane, 3.6% of butane, 1.8% of $C_{5+}$ hydrocarbons, 0.9% of nitrogen, and 0.18% of carbon dioxide is supplied via conduit 1 at a temperature of 311° K. after compression to 51.4 bar. After being cooled in heat exchanger 2 to 234° K., a condensate is obtained containing, besides 44.2% of methane and 0.2% each of nitrogen and carbon dioxide, the $C_{2+}$ hydrocarbons to be separated from the natural gas. The uncondensed proportion, having a methane concentration of above 91%, is then cooled to 214° K. in heat exchanger 9 to produce a condensate containing about 64% of methane, 0.3% each of nitrogen and carbon dioxide and, moreover, most of the previously uncondensed $C_{2+}$ hydrocarbons. This condensate is subcooled in heat exchanger 9 and, after expansion to the rectifying pressure of 17 bar, introduced at a temperature of 172° K. to the head of the rectifying column 7.

The gaseous fraction obtained in separator 11, having a $C_{2+}$ proportion of now merely 5.3%, is engine expanded in turbine 15 to a pressure of 17 bar, resulting in a temperature of 174° K. at the turbine outlet.

In the bottom of rectifying column 7, a $C_{2+}$ fraction is obtained at 299° K. which is contaminated merely by 0.7% of methane and 0.4% of carbon dioxide. The $C_{2+}$ yield of the process is 96.5%.

The fraction withdrawn from the head of rectifying column 7 contains 97.3% of methane, 1.3% of ethane, 0.1% of propane, 0.1% of carbon dioxide, and 1.2% of nitrogen, constituting a low $C_{2+}$ loss.

After being heated in heat exchangers 9 and 2 to 304° K., this gas is fed to the turbine 21 under a pressure of 16.6 bar and expanded to 4.3 bar, the temperature dropping to 234° K. After being reheated in heat exchanger 2, this gas is finally discharged at 304° K. and under a pressure of 4 bar.

The power output of turbines 15 and 21 is, in this process, 208 kW and 472 kW, respectively. This energy can be utilized, for example, for compression of the natural gas prior to its fractionation.

In order to emphasize the essential advantages as compared with the process known from U.S. Pat. No. 4,274,850, comparative calculations were performed, based on a gas having the same composition and quantity as in the above-described example. It was found that, for supplying the refrigeration requirement of the process, it is necessary to effect compression of the raw gas stream conducted via conduit 1 to 61 bar (instead of 51.4 bar as in the process of this invention), resulting in a considerable additional expenditure of energy. Furthermore, a substantially lower turbine power output is obtained compared to the process of this invention, since, during expansion of the raw gas and/or of the overhead product of the rectification, turbine outputs are obtained of 312 and 216 kW, respectively, i.e., a total of 528 kW, compared to 680 kW obtained by this invention. In addition, less apparatus parts are required in the process of this invention, i.e., instead of the three heat exchangers and separators in the prior art process, only two heat exchangers and separators.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{2+}$ hydrocarbon fraction from natural gas under pressure in a rectification column wherein the values for the temperature and the pressure required for the rectification step are obtained by heat exchange and two-stage engine expansion and wherein the rectification step is performed between a first expansion stage and a second expansion stage, the improvement which comprises cooling the natural gas to be fractionated; passing the resultant cooled natural gas to a first phase separator to saparate condensate from the cooled natural gas to be fractionated; pressure reducing the condensate from said first phase separator and delivering the resultant pressure reduced condensate to the rectification column; passing the cooled natural gas from said first phase separator to a second phase separator to separate condensate from the cooled natural gas; pressure reducing resultant separated condensate from said second phase separator and delivering the resultant pressure reduced condensate to the rectification column; engine expanding the cooled natural gas from said second phase separator in said first expansion stage to produce the peak cold required for the rectification step; withdrawing an overhead product from the rectification step; heating said overhead product to about the inlet temperature of the natrual gas to be fractonated by indirect heat exchange with the natural gas to be cooled; engine expanding resultant heated overhead product in said second expansion stage thereby cooling said overhead product; and heating resultant cooled overhead product to approximately the inlet temperature of the natural gas to be fractionated by indirect heat exchange with the natural gas to be cooled.

2. A process according to claim 1, wherein said overhead product is introduced into the second expansion stage at a temperature of between 260° and 310° K. and the gas is cooled during expansion by 50°–90° K.

3. A process according to claim 2, wherein the rectification is conducted under a pressure of 10–22 bar.

4. A process according to claim 1, wherein said overhead product is introduced into the second expansion stage at a temperature of between 270° and 305° K. and the gas is cooled during expansion by 50°–90° K.

5. A process according to claim 4, wherein the rectification is conducted under a pressure of 15–18 bar.

6. A process according to claim 1, wherein the rectification is conducted under a pressure of 10–22 bar.

7. A process according to claim 1, wherein the rectification is conducted under a pressure of 15–18 bar.

8. A process according to claim 1, wherein the first condensate separation is conducted after cooling of the natural gas in heat exchange against engine-expanded overhead product.

9. A process according to claim 8, further comprising subcooling the condensate separated in said second phase separator before said condensate is fed to the rectification column.

10. A process according to claim 9, wherein the subcooled condensate is introduced into the rectification column at the head, above the feed point for the engine-expanded natural gas.

11. A process according to claim 10, wherein the condensate separated in said second phase separator is subcooled by about 30°–45° K.

12. A process according to claim 8, wherein said overhead product is introduced into the second expansion stage at a temperature of between 270° and 305° K. and the gas is cooled during expansion by 50°–90° K.

13. A process according to claim 12, wherein the rectification is conducted under a pressure of 10–22 bar.

14. A process according to claim 1, further comprising subcooling the condensate separated in said second phase separator before said condensate is fed to the rectification column.

15. A process according to claim 14, wherein the subcooled condensate is introduced into the rectification column at the head, above the feed point for the engine-expanded natural gas.

16. A process according to claim 15, wherein the rectification is conducted under a pressure of 10–22 bar.

17. A process according to claim 16, wherein said overhead product is introduced into the second expansion stage at a temperature of between 260° and 310° K. and the gas is cooled during expansion by 50°–90° K.

18. A process according to claim 17, wherein the condensate separated in said second phase separator is subcooled by about 30°–45° K.

19. A process according to claim 15, wherein said overhead product is introduced into the second expansion stage at a temperature of between 260° and 310° K. and the gas is cooled during expansion by 50°–90° K.

20. A process according to claim 14, wherein said overhead product is introduced into the second expansion stage at a temperature of between 260° and 310° K. and the gas is cooled during expansion by 50°–90° K.

21. A process according to claim 14, wherein the condensate separated in said second phase separator is subcooled by about 30°–45° K.

* * * * *